United States Patent [19]

Larock

[11] Patent Number: 4,948,905

[45] Date of Patent: Aug. 14, 1990

[54] SYNTHESIS OF VINYL LACTONES

[75] Inventor: Richard C. Larock, Ames, Iowa

[73] Assignee: Iowa State University Reasearch Foundation, Inc., Ames, Iowa

[21] Appl. No.: 408,894

[22] Filed: Sep. 18, 1989

[51] Int. Cl.$^5$ .................. C07D 307/26; C07D 309/16
[52] U.S. Cl. ..................................... 549/326; 549/273
[58] Field of Search ............................... 549/326, 273

[56] References Cited

U.S. PATENT DOCUMENTS

| | | | |
|---|---|---|---|
| 2,361,968 | 11/1944 | Ruzicka | 549/115 |
| 3,227,732 | 1/1966 | Tschesche et al. | 549/326 |
| 3,332,963 | 7/1967 | Cramer | 549/326 |
| 3,531,501 | 9/1970 | Herringa et al. | 549/326 |
| 4,167,513 | 9/1979 | Musco et al. | 549/326 |
| 4,175,187 | 11/1979 | Heck | 544/170 |
| 4,225,704 | 9/1980 | Heine et al. | 542/441 |
| 4,247,468 | 1/1981 | Cleveland | 549/326 |
| 4,413,133 | 11/1983 | Damin et al. | 549/265 |
| 4,602,006 | 7/1986 | Krantz et al. | 514/63 |
| 4,734,511 | 3/1988 | Inagaki et al. | 549/273 |

FOREIGN PATENT DOCUMENTS 58-69820 4/1983 Japan .
1148043 4/1969 United Kingdom .

OTHER PUBLICATIONS

"Synthesis of Vinylic Lactones via Palladium-Catalyzed . . . ", Tetrahedron Lett. 29(49)6399–402 (1988), Larock and Leack.

Primary Examiner—Anton H. Sutto
Assistant Examiner—Celia Chang
Attorney, Agent, or Firm—Zarley, McKee, Thomte, Voorhees & Sease

[57] ABSTRACT

Synthesis of vinyl lactones by means of palladium catalyzed coupling of vinylic halides or triflates and certain unsaturated carboxylic acids.

14 Claims, No Drawings

SYNTHESIS OF VINYL LACTONES

GRANT REFERENCE

The invention described herein was made in part in the course of work under a grant from the National Institutes of Health, No. GM24254.

BACKGROUND OF THE INVENTION

γ-Alkenyl-γ-butyrolactones and δ-alkenyl-δ-valerolactones are present in nature and have proven useful as intermediates in organic synthesis. Many of these lactones are of keen biological interest. For example, some of the lactones are known to be odor-bearing components of many plants, and as such have found wide industrial use in the perfume industry. Certain lactones are also useful as solvents, paint removers, vapor sterilants, and disinfectants. It therefore can be seen that there is a continuing need for the development of processes of preparing these useful compounds by convenient and efficient syntheses.

It is a primary objective of the present invention to provide an improved one pot process for the preparation of many vinylic lactones.

A further object of the present invention is to prepare vinylic lactones from vinylic halides or triflates when reacted with unsaturated carboxylic acids.

A further objective of the present invention is to prepare vinylic lactones by a process which avoids the use of mercury salts, as used in an earlier reported process of the inventor, Larock et al., *Tetrahedron Letters* 1987, 28, 4977.

The method and manner of accomplishing each of the above objectives as well as others will become apparent from the detailed description of the invention which follows hereinafter.

SUMMARY OF THE INVENTION

Vinylic halides or triflates are reacted with unsaturated carboxylic acids, such as 3-butenoic or 4-pentenoic acid in the presence of a palladium(II) or palladium(0) catalyst under mild reaction conditions to prepare the corresponding vinylic lactones by an intramolecular π-allylpalladium displacement process.

DETAILED DESCRIPTION OF THE INVENTION

The process of the patent may be summarized by the following equation.

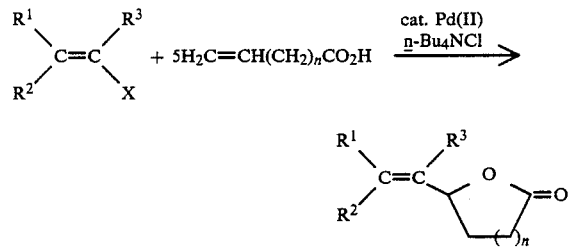

In word description the vinylic lactones are prepared by reacting a vinylic halide or triflate with an unsaturated carboxylic acid. $R^1$, $R^2$, and $R^3$ represent $C_1$ to $C_{12}$ alkyl moieties or an aryl. X represents a halide or a triflate (trifluoromethanesulfonyloxy). Preferably X is a halide. Preferably $R^1$, $R^2$, and $R^3$ are $C_1$ to $C_8$ alkyl. The alkyl group may have functional substitution if desired. The substituted functionality may include ketone, ester, nitrile, amide, ether, silyl ether.

The unsaturated carboxylic acid chain length is represented by the number of repeating methylene units and preferably "n" is one or two. There may be some substitution on the chain of the unsaturated carboxylic acid, but the terminal carbon should remain free from substitution. Typical examples of unsaturated carboxylic acids which can be employed in these reactions include 3-butenoic acid, 4-pentenoic acid, and 2-methyl-3-butenoic acid. It is desired that an excess of unsaturated carboxylic acid be employed since yields seem to be increased. Generally anywhere from 2 to 5 times the stoichiometric amount of carboxylic acid is preferred.

The reaction is run in a polar solvent. There is no criticality for the polar solvent, and any solvent which will dissolve the reactive is suitable. Typical solvents include dimethylformamide (DMF), dimethylacetamide (DMA), acetonitrile or dimethylsulfoxide (DMSO).

The reaction affords increased yields if it is conducted in the presence of a base. Suitable bases include carbonate bases such as sodium or potassium bicarbonate or carbonate, and also tertiary amine bases, such as diisopropylethylamine or triethylamine. Typically the amount of base may be from 3-5 equivalents. Lowering the amount of base to lower levels will decrease the yield.

The reaction is a palladium-promoted intramolecular x-allylpalladium displacement process, and thus it must be conducted in the presence of a palladium catalyst. The catalyst may be palladium chloride, lithium palladium chloride, palladium acetate or nitrate or a palladium(O) catalyst. The palladium(O) catalyst employed is also not critical, tetrakis(triphenylphosphine)palladium(O) or bis(dibenzylideneacetone)palladium can be employed. The amount of catalyst employed is not critical, as long as it is a catalytically effective amount.

The amount of palladium catalyst can vary from 0.1% up to 5% by weight of the reactants.

For reasons that are not completely understood, it is also preferred from the standpoint of increased yields and faster reactions if the reaction is run in the presence of tetra-n-butylammonium chloride. The amount should be an equivalent amount to the amount of initial vinylic halide reactant.

Temperature and pressure are not critical, and generally the reaction may be run at from about 40° C. to about 120° C., more typically from about 60° C. to about 90° C. At 80° C. the reaction seems to go as near to completion as it will in about 24 hours. About 2 hours should be sufficient time at 120° C.

When the reaction is conducted in the manner hereinbefore described, reaction yields of the vinylic lactones can be achieved at levels as high as 70% in some instances. This is significant in comparison with other procedures for such synthesis.

EXAMPLES

The following examples are offered to illustrate but not limit, the process of this invention.

Examples 1-17 are listed in the Table below. Generally all of the reactions were run under similar conditions. In particular they were run by heating the alkenyl halide or triflate (0.5 mmol), the unsaturated acid (2.5 mmol), n-Bu$_4$NCl (0.5 mmol), i-Pr$_2$NEt (2.25 mmol), and Pd(OAc)$_2$ (0.025 mmol) in 2 ml of DMF at 80° C. for 20 hours in a sealed vial.

TABLE I
Synthesis of Vinylic Lactones

| | Unsaturated Acid | Alkenyl Halide or Triflate | Lactone | | % Isolated Yield |
|---|---|---|---|---|---|
| | $H_2C=CHCH_2CO_2H$ | | (R)(H)C=C(H)(R)—lactone where R on ring | | |
| 1 | | E- $\underline{n}$-C$_4$H$_9$CH=CHI | $\underline{n}$-C$_4$H$_9$ | | 66,73$^b$ |
| 2 | | Z- $\underline{n}$-C$_4$H$_9$CH=CHI | $\underline{n}$-C$_4$H$_9$ | | 59 |
| 3 | | E- $\underline{n}$-C$_4$H$_9$CH[OSiMe$_2$(t-Bu)]CH=CHI | $\underline{n}$-C$_4$H$_9$CHOSiMe$_2$(t-Bu) | | 41 |
| 4 | | E- (CH$_3$)$_3$CCH=CHI | (CH$_3$)$_3$C | | 60 |
| 5 | | E- C$_6$H$_5$CH=CHI | C$_6$H$_5$ | | 49,54$^b$ |
| 6 | | E- C$_6$H$_5$CH=CHBr | C$_6$H$_5$ | | 53$^c$ |
| 7 | | (CH$_3$)$_2$C=CHI | (CH$_3$)(CH$_3$)C=C lactone | | 61 |
| 8 | | $H_2C=CBrC_6H_5$ | C$_6$H$_5$ | | 25$^c$ |
| 9 | | $H_2C=CI(CH_2)_3CH_3$ | $\underline{n}$-C$_4$H$_9$ | | 30 |
| 10 | | cyclohexenyl-OTf | cyclohexenyl lactone | | 58$^c$ |
| | $H_2C=CHCH(CH_3)CO_2H$ | | (R)(H)C=C(H)— lactone with CH$_3$ | trans/cis | |
| 11 | | E- $\underline{n}$-C$_4$H$_9$CH=CHI | $\underline{n}$-C$_4$H$_9$ | 2.6/1 | 59 |
| 12 | | E- C$_6$H$_5$CH=CHBr | C$_6$H$_5$ | 2.3/1 | 55 |
| | $H_2C=CH(CH_2)_2CO_2H$ | | (R)(H)C=C(H)—6-membered lactone | | |
| 13 | | E- $\underline{n}$-C$_4$H$_9$CH=CHI | $\underline{n}$-C$_4$H$_9$ | | 61$^d$ |
| 14 | | E- $\underline{n}$-C$_4$H$_9$CH[OSiMe$_2$(t-Bu)]CH=CHI | $\underline{n}$-C$_4$H$_9$CHOSiMe$_2$(t-Bu) | | 39$^d$ |
| 15 | | E- (CH$_3$)$_3$CCH=CHI | (CH$_3$)$_3$C | | 63$^d$ |
| 16 | | E- C$_6$H$_5$CH=CHI | C$_6$H$_5$ | | 21$^d$ |
| 17 | | E- C$_6$H$_5$CH=CHBr | C$_6$H$_5$ | | 26$^d$,27$^{c,d}$ |

$^b$Reaction run on a 1.0 mmol scale.
$^c$Reaction run at 100° C.
$^d$Reaction run in acetonitrile using 5% Pd(dba)$_2$.

What is claimed is:

1. A method of synthesis of vinylic lactones, comprising: reacting a vinyl compound of the formula:

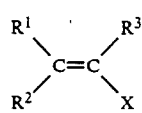

wherein X equals a halide or a triflate, with an unsaturated carboxylic acid of the formula:

wherein "n" is selected from the numbers 1 and 2, in the presence of a palladium catalyst to provide a vinylic lactone.

2. The method of claim 1 wherein the reaction is conducted in the presence of an excess of the unsaturated carboxylic acid.

3. The method of claim 1 wherein R$^1$, R$^2$ and R$^3$ are selected from the group consisting of C$_1$ to C$_{12}$ alkyl and aryl.

4. The method of claim 3 wherein R$^1$, R$^2$ and R$^3$ are selected from the group consisting of C$_1$ to C$_8$ alkyl.

5. The method of claim 1 wherein "n" is one.

6. The method of claim 1 wherein "n" is two.

7. The method of claim 1 wherein said method is conducted in the presence of a polar solvent.

8. The method of claim 7 wherein the polar solvent is dimethylformamide.

9. The method of claim 7 wherein the polar solvent is acetonitrile.

10. The method of claim 7 wherein the method is conducted in the presence of a base.

11. The method of claim 10 wherein the base is diisopropylethylamine.

12. The method of claim 10 wherein the base is sodium carbonate.

13. The method of claim 1 wherein the reaction is conducted at a temperature of from about 40° C. to about 120° C. for from about 2.0 hours to about 24.0 hours.

14. The method of claim 13 wherein the reaction is conducted at a temperature of from about 60° C. to about 80° C. for from about 4.0 hours to about 20 hours.

* * * * *